（12）United States Patent
Chen et al.

(10) Patent No.: US 9,457,000 B2
(45) Date of Patent: Oct. 4, 2016

(54) GAMMA-POLYGLUTAMIC ACID-BASED INTRAOCULAR IRRIGATION SOLUTIONS

(71) Applicant: NATIONAL HEALTH RESEARCH INSTITUTES, Miaoli County (TW)

(72) Inventors: Yu-Chun Chen, Miaoli County (TW); Wen-Yu Su, Miaoli County (TW); Yen-Hsien Lee, Miaoli County (TW); Ko-Hua Chen, Taipei (TW); Feng-Huei Lin, Miaoli County (TW)

(73) Assignee: NATIONAL HEALTH RESEARCH INSTITUTES, Miaoli County (TW)

( * ) Notice: Subject to any disclaimer, the term of this patent is extended or adjusted under 35 U.S.C. 154(b) by 60 days.

(21) Appl. No.: 13/918,963

(22) Filed: Jun. 16, 2013

(65) Prior Publication Data

US 2013/0273186 A1    Oct. 17, 2013

Related U.S. Application Data

(62) Division of application No. 13/081,138, filed on Apr. 6, 2011, now abandoned.

(60) Provisional application No. 61/322,738, filed on Apr. 9, 2010.

(51) Int. Cl.
    *A61K 31/74*   (2006.01)
    *A61K 31/198*  (2006.01)
    *A61K 31/765*  (2006.01)

(52) U.S. Cl.
     CPC .............. *A61K 31/198* (2013.01); *A61K 31/74* (2013.01); *A61K 31/765* (2013.01)

(58) Field of Classification Search
     None
     See application file for complete search history.

(56) References Cited

U.S. PATENT DOCUMENTS

| 4,620,979 A     | * | 11/1986 | Schachar | ................... 424/678 |
| 2006/0177524 A1 | * | 8/2006  | Armitage | ............ A61K 9/0048 |
|                 |   |         |          | 424/717 |

FOREIGN PATENT DOCUMENTS

| WO | 9925864 A2     | 5/1999 |
| WO | 2009/088118 A1 | 7/2009 |
| WO | 2009/088119 A1 | 7/2009 |

OTHER PUBLICATIONS

Nationwide Childrens (retrieved from http://www.nationwidechildrens.org/swelling-bodys-reaction-to-injury on May 14, 2015, 2 pages).*
Bae et al "Effect of Ultra High Molecular Weight Poly-gamma-glutamic acid from Bacillus subtillts on corneal wound healing" J. of Microbiology and Biotechnology, vol. 20, No. 4, Jan. 30, 2010, pp. 803-808.

* cited by examiner

*Primary Examiner* — Karlheinz R Skowronek
*Assistant Examiner* — Ronald Niebauer
(74) *Attorney, Agent, or Firm* — Hsiu-Ming Saunders; Intellectual Property Connections, Inc.

(57) ABSTRACT

Ophthalmic irrigating solutions are disclosed. The ophthalmic irrigating solution comprises: a) γ-polyglutamic acid (γ-PGA) and/or salt thereof in an amount effective to increase the viscosity of the irrigating solution, and b) an ophthalmically acceptable aqueous vehicle for the γ-PGA and/or salt thereof. Also disclosed is a method of irrigating ocular tissues of a patient, in which the method comprises introducing to the ocular tissues of the patient an ophthalmic irrigating solution comprising γ-PGA) and/or salt thereof in an amount sufficient to irrigate the ocular tissues of the patient.

20 Claims, 9 Drawing Sheets

GAMMA-POLYGLUTAMIC ACID-BASED INTRAOCULAR IRRIGATION SOLUTIONS

REFERENCE TO RELATED APPLICATION

The present application is a Divisional Application of U.S. application Ser. No. 13/081,138, filed Apr. 6, 2011, which status is pending, and claim priority to U.S. Provisional Application Ser. No. 61/322,738, filed Apr. 9, 2010, all of which are herein incorporated by reference in their entireties.

FIELD OF THE INVENTION

The present invention relates generally to ocular solutions, and more specifically to ocular irrigating solutions.

BACKGROUND OF THE INVENTION

Irrigating solutions are widely used in intraocular surgical procedures, such as phacoemulsification, vitrectomy surgery and glaucoma surgery. Phacoemulsification is a surgery to remove the lens of the eye that has developed an opacification, which is referred to as a cataract. Vitrectomy is a surgery to remove some or all of the vitreous humor from an eye. Glaucoma surgery is associated with a laser treatment or making a cut in the eye to reduce the intraocular pressure. In Taiwan, according to a report of National Health Insurance Department about 150,000 ocular surgical procedures were performed annually. The effect of intraocular surgery is related to the irrigating solution used. An improper irrigating solution may cause damages to cornea or lens, resulting in poor vision, blind spots and even loss of vision.

A desired irrigating solution is supposed to have a composition that is close to aqueous humor and an osmolarity of between 290 mOsm and 320 mOsm. The major function of irrigating solutions is for maintaining endothelium cell integrity, corneal thickness and retinal tissue. Moreover, an appropriate irrigating solution should preserve the viability of corneal endothelial cells during cataract surgery, provide an energy source (i.e., glucose), maintain appropriate tonicity and electrolyte concentration, and protect corneal endothelium cells from fluctuation of pH value.

Balanced Salt Solution (BSS®) and BSS PLUS® have been frequently used for intraocular irrigation. The composition of BSS PLUS® is close to that of the aqueous humor. Basically, the composition of BSS PLUS® has four parts: 1) adequate buffer (i.e., bicarbonate), 2) energy source (i.e., glucose). 3) stable pH value between 7 and 8 (i.e., HEPES). 4) antioxidant agent (i.e., glutathione) However, these intraocular irrigating solutions are not effective enough to protect corneal (endothelial) cells, which are most liable to sustain physical damage in ophthalmic operations. Studies have indicated that a sophisticated intraocular surgery, such as phacoemulsification, may cause potential complications. Some possible reasons for causing complications include the mechanical effects of ultrasound, physical trauma caused by nonaspirated lens fragments, heat production and even osmotic irregularities caused by the irrigating solution. All of these may result in damages to corneal endothelium and even may have the risk of leading to irreversible bullous keratopathy.

Therefore, a heretofore unaddressed need exists in the art to address the aforementioned deficiencies and inadequacies, especially in connection with development of ocular irrigating solutions with an improved functionality to protect intraocular tissues, particularly conical (endothelial) cells.

SUMMARY OF THE INVENTION

In one aspect, the invention relates to a method of irrigating ocular tissues of a patient. The method comprises introducing to the ocular tissues of the patient an ophthalmic irrigating solution in an amount sufficient to irrigate the ocular tissues of the patient, in which the solution comprises: a) γ-polyglutamic acid (γ-PGA) and/or salt thereof in an amount effective to increase the viscosity of the solution; and b) an ophthalmically acceptable aqueous vehicle for the γ-PGA and/or salt thereof.

In another aspect, the invention relates to an ophthalmic irrigating solution comprising: γ-polyglutamic acid (γ-PGA) and/or salt thereof in an amount effective to increase the viscosity of the irrigating solution; and b) an ophthalmically acceptable aqueous vehicle for the γ-PGA and/or salt thereof.

Further in another aspect, the invention relates to a pharmaceutical kit comprising: a) an ophthalmic irrigating solution as aforementioned; and b) a package insert containing printed instructions for irrigating ocular tissues of a patient.

Yet in another aspect, the invention relates to a method of reducing stress-induced damage to ocular tissues of a patient dining eye surgery. The method comprises introducing to the ocular tissues of the patient during the eye surgery an ophthalmic irrigating solution in an amount sufficient to irrigate the ocular tissues of the patient, in which the irrigating solution comprises: a) γ-polyglutamic acid (γ-PGA) and/or salt thereof in an amount effective to increase the viscosity of the solution; and b) an ophthalmically acceptable aqueous vehicle for the γ-PGA and/or salt thereof.

These and other aspects will become apparent from the following description of the preferred embodiment taken in conjunction with the following drawings, although variations and modifications therein may be affected without departing from the spirit and scope of the novel concepts of the disclosure.

The accompanying drawings illustrate one or more embodiments of the invention and, together with the written description, serve to explain the principles of the invention. Wherever possible, the same reference numbers are used throughout the drawings to refer to the same or like elements of an embodiment.

DETAILED DESCRIPTION OF THE INVENTION

Definitions

Figure 1A:
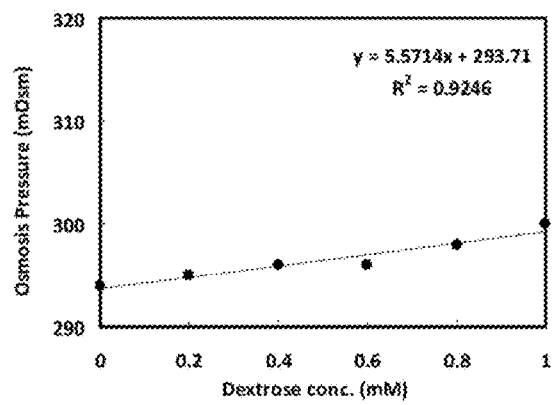
FIGS. 1A-1C show the effects of γ-PGA and dextrose concentrations on the osmolarity of the irrigating solution.

The terms used in this specification generally have their ordinary meanings in the art, within the context of the invention, and in the specific context where each term is used. Certain terms that are used to describe the invention are discussed below, or elsewhere in the specification, to provide additional guidance to the practitioner regarding the description of the invention. For convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and in no way limits the scope and meaning of the invention or of any exemplified term. Likewise, the invention is not limited to various embodiments given in this specification.

Unless otherwise defined, all technical and scientific terms used herein have the same meaning as commonly understood by one of ordinary skill in the art to which this invention pertains. In the case of conflict, the present document, including definitions will control.

As used herein, "around", "about" or "approximately" shall generally mean within 20 percent, preferably within 10 percent, and more preferably within 5 percent of a given value or range. Numerical quantities given herein are approximate, meaning that the term "around", "about" or "approximately" can be inferred if not expressly stated.

As used herein, when a number or a range is recited, ordinary skill in the art understand it intends to encompass an appropriate, reasonable range for the particular field related to the invention.

By a viscosity of 0.32 to 50 centipoise it meant that all hundredth, tenth and integer unit amounts within the range are specifically disclosed as part of the invention. Thus, 0.32, 0.33, 0.34 . . . and 0.7, 0.8, 0.9 and 1, 2, 3, 4 . . . 47, 48, 49 and 50 centipoise unit amounts are included as embodiments of this invention.

By an osmolarity of 290 to 320 mOsm it meant that all integer unit amounts within the range are specifically disclosed as part of the invention. Thus, 290, 291, 292 . . . and 317, 318, 319 and 320 mOsm unit amounts are included as embodiments of this invention.

By a refractive index of 1.330 to 1.344 it meant that all thousandth unit amounts within the range are specifically disclosed as part of the invention. Thus, 1.330, 1.331, 1.332 . . . and 1.340, 1.341, 1.342, 1.343 and 1.344 unit amounts are included as embodiments of this invention.

By a molecular weight of 10,000 to 2,000,000 Daltons it meant that all integer unit amounts within the range are specifically disclosed as part of the invention. Thus, 10,000, 10,001, 10,002 . . . and 1,999,997, 1,999,998, 1,999,999 and 2,000,000 Daltons unit amounts are included as embodiments of this invention.

By 0.2~1% (w/v) it meant that all tenth and integer unit amounts within the range are specifically disclosed as part of the invention. Thus, 0.2, 0.3, 0.4 . . . and 0.7, 0.8, 0.9 and 1% unit amounts are included as embodiments of the invention.

As used herein, "γ-PGA" shall generally mean "gamma-polyglutamic acid and/or salt thereof" or "gamma-polyglutamate." Glutamic acid has 2 carboxyl groups. One of them, γ-carboxyl group is linked with α-amino group and PGA is formed.

The terms Gamma-Poly(glutamic acid) and Gamma-Polyglutamic acid (γ-PGA) are interchangeable.

As used herein, the term "in an effective amount to increase the viscosity of the irrigating solution" shall generally mean that the viscosity of the irrigating solution is increased in the presence of γ-PGA compared to the viscosity of the irrigating solution without the addition of γ-PGA.

Cross-linked polyglutamic acid consists of mesh structure of tens of millions by molecular weight. Compared to PGA, cross-linked PGA has higher water absorption capability. The molecular weight of cross-linked polyglutamic acid is more than 10,000,000.

As used herein, "an aqueous physiologically acceptable solution" shall generally mean but not limited to sterile saline or sterile buffered solution.

As used herein, an "antioxidant" is a molecule capable of slowing or preventing the oxidation of other molecules. Antioxidants include but not limited to glutathione, vitamin C, and vitamin E.

Osmosis is the movement, of solvent molecules through a selectively-permeable membrane into a region of higher solute concentration, aiming to equalize the solute concentrations on the two sides. Net movement of solvent is from the less-concentrated (hypotonic) to the more-concentrated (hypertonic) solution, which tends to reduce the difference in concentrations. This effect can be countered by increasing the pressure of the hypertonic solution, with respect to the hypotonic. The osmotic pressure is defined to be the pressure required to maintain an equilibrium, with no net movement of solvent. The osmotic pressure depends on the molar concentration of the solute but not on its identity. Osmosis is important in biological systems, as many biological membranes are semipermeable.

Osmolarity is the measure of solute concentration, defined as the number of osmoles (Osm) of solute per liter (L) of solution (osmol/L or Osm/L). The osmolarity of a solution is usually expressed as Osm/L. Osmolarity measures the number of osmoles of solute particles per unit volume of solution.

The invention relates to the discovery of the viscoelastic material poly-γ-glutamic acid (γ-PGA) as an additional ingredient in irrigating solutions to reduce injury caused by eye surgery. Dispersive viscoelastic materials have the positive effect on protecting intraocular tissues during phacoemulsification and aspiration (PEA). Viscoelastic materials can reduce the turbulence within the anterior and posterior chambers of the eye and help contain the movement of tissue fragments and air bubbles within the eye. Besides, such kinds of viscoelastic materials can facilitate the removal of lens fragments and make it easier for a surgeon to track the fragments with the tip of a surgical hand piece.

Poly-γ-glutamic acid (γ-PGA), a natural polymer of the amino acid glutamic acid (GA), is synthesized by several bacteria (all Gram-positive), one archaea and one eukaryote. The structure of PGA is shown below:

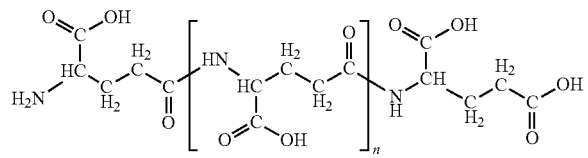

Poly-γ-glutamic acid has a molecular weight ranging from about 10,000 up to 2 millions. It can be produced to meet the requirements of different applications. It is well known for its application in food industry. γ-PGA is a major composition of mucilage of "natto" (one kind of traditional Japan food), which was first discovered by Ivnovics as a capsule of *Bacillus anthracis* in 1937, γ-PGA is a unique polyanionic polymer composed of D form and/or L form glutamic acid residues connected by γ-amide bonds (between the α-amino and γ-carboxylic groups). It is a hydrophilic, viscous, biodegradable and non-toxic biomaterial. Due to the unique properties on ion trapping and high water absorbance, it has been widely used in various applications, such as metal chelate, absorbent, cryoprotectant, ageing inhibitor, drug, carrier and humectant. γ-PGA has been widely used as a biomaterial with a fine swelling ability during the past few years. The biocompatibility makes it practicable for use in clinical fields such as bioglue, tissue engineering and drug delivery systems.

The invention relates to the discovery that γ-PGA has the ability to adjust the osmolarity and viscosity of an ophthalmically acceptable irrigating solution. Adequate osmolarity and slight viscosity of an ophthalmic irrigating solution should be able to reduce complications and injury of cornea. The present invention relates to use of γ-PGA as an additive for an ophthalmically acceptable irrigating solution or a surgical solution to provide the anterior and posterior chambers of the eye with protections during surgical procedures that require irrigation.

γ-PGA serves as an agent for adjusting the osmolarity and avoiding edema phenomena of the tissue. The osmolarity of the ophthalmically acceptable irrigating solution in the presence of γ-PGA is in the range of 290~320 mOsm. The high molecular weight (1020 k Daltons) γ-PGA has the ability to adjust the viscosity of the irrigating solution. An optimal viscosity can reduce tissue injury caused by phacoemulsification.

Various types of vehicles for the γ-PGA may be utilized. However, the vehicle preferably contains electrolytes, a buffer (e.g., bicarbonate, phosphate or a combination thereof), and an energy source. These agents help to maintain the normal function of corneal tissues during the surgical procedure and promote a rapid recovery of visual acuity subsequent to the surgery. However, the invention is not limited relative to the types of balanced salt solutions or other electrolyte/nutrient solutions that may be utilized to form the irrigating solutions described herein.

In one aspect, the invention relates to a method of irrigating ocular tissues of a patient. The method comprises introducing to the ocular tissues of the patient an ophthalmic irrigating solution in an amount sufficient to irrigate the ocular tissues of the patient, in which the solution comprises: a) γ-polyglutamic acid (γ-PGA) and/or salt thereof in an amount effective to increase the viscosity of the solution; and b) an ophthalmically acceptable aqueous vehicle for the γ-PGA and/or salt thereof.

In another aspect, the invention relates to an ophthalmic irrigating solution comprising: a) γ-polyglutamic acid (γ-PGA) and/or salt thereof in an amount effective to increase the viscosity of the irrigating solution; and b) an ophthalmically acceptable aqueous vehicle for the γ-PGA and/or salt thereof.

Further in another aspect, the invention relates to a pharmaceutical kit comprising: a) an ophthalmic irrigating solution as aforementioned; and b) an a package insert containing printed instructions for irrigating ocular tissues of a patient.

In one embodiment of the invention, the irrigating solution has a viscosity of 0.32 to 50, or 0.32 to 30, or 0.32 to 3.93 centipoise.

In another embodiment of the invention, the irrigating solution has an osmolarity of 290 to 320 mOsm per Liter.

In another embodiment of the invention, the irrigating solution has a viscosity of 0.32 to 50, or 0.32 to 30, or 0.32 to 3.93 centipoise and an osmolarity of 290 to 320 mOsm per Liter.

In another embodiment of the invention, the irrigating solution has a refractive index of 1.330 to 1.344.

In another embodiment of the invention, the irrigating solution does not contain cross-linked polyglutamic acid and has no additional polyamino acid or polymer.

In another embodiment of the invention, the ophthalmically acceptable aqueous vehicle comprises a balanced salt solution containing electrolytes, a buffer and an energy source.

In another embodiment of the invention, the concentration of γ-PGA in the ophthalmic irrigating solution ranges from 0.2~1% or 0.2~0.8% (w/v).

In another embodiment of the invention, the γ-PGA has a molecular weight of 10,000 to 2,000,000 Daltons, or 1,000,000 to 2,000,000 Daltons.

Further in another embodiment of the invention, the ophthalmically acceptable aqueous vehicle further comprises an antioxidant.

Yet in another aspect, the invention relates to a method of reducing stress-induced damage to ocular tissues of a patient during eye surgery. The method comprises introducing to the ocular tissues of the patient during the eye surgery an ophthalmic irrigating solution in an amount sufficient to irrigate the ocular tissues of the patient, in which the irrigating solution comprises a) γ-polyglutamic acid (γ-PGA) and/or salt thereof in an amount effective to increase the viscosity of the solution; and b) an ophthalmically acceptable aqueous vehicle for the γ-PGA and/or salt thereof.

In one embodiment of the invention, the eye surgery includes surgical vitrectomy, cataract extraction, lens aspiration, anterior segment reconstruction and phacoemulsification.

EXAMPLES

Without intent to limit the scope of the invention, exemplary instruments, apparatus, methods and their related results according to the embodiments of the present invention are given below. Note that titles or subtitles may be used in the examples for convenience of a reader, which in no way should limit the scope of the invention. Moreover, certain theories are proposed and disclosed herein; however, in no way they, whether they are right or wrong, should limit the scope of the invention so long as the invention is practiced according to the invention without regard for any particular theory or scheme of action.

Materials And Methods

Materials And Reagent

All materials and reagents used were purchased from Sigma-Aldrich, Inc. (St. Louis, Mo., USA) unless otherwise stated. Poly-γ-glutamate (molecular weight 1020 k Da) was purchased from VEDAN Enterprise Corporation. Osmometer standards were obtained from Advanced Instruments, Inc. (Norwood, Mass., USA).

Antibiotic, trypsin and fetal bovine serum were obtained from Invitrogen (Carlsbad, Calif.). Flasks and culture well/dishes were obtained from Orange Scientific (Braine-l'Alleud, Belgium). Qick Cell Proliferation Assay Kit was procured from BioVision (CA, USA) and cytotoxicity assay was purchased from Promega (CytoTox 96 Assay kit, WI, USA). Bovine cornea endothelial cells (bCE cells) and human retina pigmented epithelium cells (hRPE cells) were obtained from the National Center for Cell Sciences (Food Industry Research and Development Institute, Hsinchu, Taiwan).

Methods

Osmolarity Evaluation of the Irrigating Solution

The osmolarity of the solution was measured in duplicates using a 3D3 Single-Sample Osmometer manufactured by Advanced instrument, Co., Inc. To investigate the effect of γ-PGA, irrigating solutions containing various concentrations of γ-PGA, 0.2%, 0.4%, 0.6%, 0.8%, 1% and control (without γ-PGA) were prepared. Calibration standards (100 and 1500 mOsm per Liter) were used to calibrate the performance of the osmometer. The pH value of the γ-PGA-containing irrigating solution was 7.4±0.1. Sodium bicarbonate was used as a pH buffer and double distilled water was used to make irrigating solutions.

Viscosity Evaluation of the Irrigating Solution

A HAAKE RheoStress 600 (Thermo Fisher Scientific Inc., Waltham, Mass., USA) instrument with parallel plate geometry was used to evaluate the viscosity of the irrigating solution. The temperature was controlled by control units. Two working temperatures, room temperature (25° C.) and body temperature (37° C.), were evaluated. The gap height between the upper (35 mm in diameter) and bottom stainless steel plates was set at 1.05 mm. Controlled rate rotation ramp mode was used to obtain the viscosity curve of the irrigating solution. The range of the shear rate was from to 1 $s^{-1}$ to 500 $s^{-1}$.

Refractive Index Evaluation of the Irrigating Solution

A DR-A1 refractometer (ATAGO, Japan) was used to measure the refractive index (RI). Irrigating solutions containing 0.2, 0.4, 0.6, 0.8 and 1% (w/v) of γ-PGA were prepared at room temperature and placed carefully on the prism. While looking through the eyepiece, the control knob was turned until the shadow line was centered in the crosshairs. The value of refractive index was taken from the digital screen.

Biocompatibility Studies of γ-PGA

Different concentrations of γ-PGA were added to culture medium to evaluate the biocompatibility. Two hundred microliters of the medium was tested on a monolayer of corneal endothelium cells and retinal pigment epithelium cells. Cells were seeded onto 96-well tissue culture plates at a cell density of $5 \times 10^3$ cells/well, allowed to adhere overnight at 37° C. under 5% carbon dioxide atmosphere. Groups including a negative control ($Al_2O_3$ extraction medium), a positive control (0.1% Triton X-100 contained medium) and experimental groups (medium with 0.4%, 0.6%, 0.8% and 1% γ-PGA) were tested in hexaplicate. After incubation at 37° C. for 24 h and 72 h, the cell viability and cytotoxicity evaluations were quantitatively assessed using Quick Cell Proliferation Assay Kit II and CYTOTOX 96® Cytotoxicity Assay.

For cell viability evaluation, the test medium after 72 h incubation was discarded and 0.2 ml of water-soluble tetrazolium-8 (WST-8) working solution was transferred into each well. After 2 h incubation, the WST-8 working solution showed color changes due to cleavage of tetrazolium salt and formation of formazan by cellular mitochondrial dehydrogenases. The viability of corneal endothelium cells and retinal pigment epithelium cells was quantitatively assessed by spectrophotometer readout at 450 nm. The reference wavelength was 650 nm.

For cytotoxicity evaluation, 0.05 ml of the incubation medium was transferred into 96-well ELSA plates, mixed with 0.05 ml of the substrate mix and incubated for 30 minutes in the dark. The tetrazolium salt in the substrate mix reacts with lactate dehydrogenase and gives a red formazan product. LDH released into the medium was quantitatively assessed by spectrophotometer readout at 490 nm. Medium (without incubation with cells) was also evaluated to serve as a culture medium background. All conical endothelium cells and retinal pigment epithelium cells were lysed with lysis solution (1% TRITON® X-100) and the $OD_{490}$ value was read. Percent cytotoxicity was expressed as follows:

$$\% \text{ Cytotoxicity} = \frac{\text{Medium } O.D. - \text{Blank } O.D.}{\text{Total Lysis } O.D. - \text{Blank } O.D.} \times 100$$

Fluorescence Staining

Cells cultured in the medium containing γ-PGA at a concentration of 0.2, 0.4, 0.6, 0.8 and 1% (w/v) for one day and 3 days were respectively stained with a LIVE/DEAD staining kit (Molecular Probes #L3224, Eugene, Oreg., USA) and photographed by using NIS Element software.

In Vivo Study of the γ-Poly(Glutamic Acid)-Based Ocular Irrigation Solution

Figure 8A:
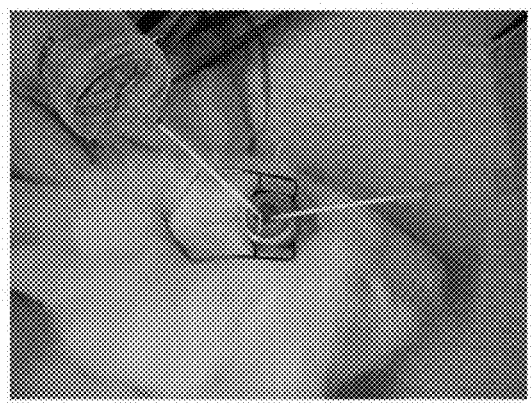
FIG. 8A shows two vein detained needles inserted into an eye of a rabbit.
Figure 8B:
FIG. 8B shows perfusion of irrigation solution by a peristaltic pump.

Six eyes of three New Zealand white rabbits (2~3 kg) were used. The surgeries were performed under general anesthesia by intramuscular injection of ketalar/Chanazine 2% (Ketamine: 22 mg/kg BW; Xylazine: 4-6 mg/kg BW). Under an operating microscope, two vein detained needles were carefully inserted through cornea without touching the lens (FIG. 8A). One of the vein detained needles was connected to a bottle full of the experimental ocular irrigating solution, and the other was connected to an empty bottle (FIG. 8B). The corneal endothelium was perfused with the irrigation solution at 37° C. by using a peristaltic pump (flow rate of 5 mL/min) (FIG. 8B) for 60 minutes. The right eye was irrigated with 0.4% (w/v) of γ-poly(glutamic acid)-based ocular irrigating solution and the left eye irrigated with a normal saline solution. Corneal thickness was measured at intervals of five to ten minutes during the course of perfusion.

Corneal Thickness Measurement

An ultrasonic pachymeter DGH 550 (DGH Technology) with a hand-held transducer was used to measure central corneal thickness. The DGH 550 is an ultrasonic pachymeter that uses echo spike techniques to measure the thickness of the cornea. Cornea thickness was measured using the Ultrasonic pachymeter at intervals of five to ten minutes during the course of perfusion.

Statistical Analysis

Statistical analysis was conducted at least in triplicate, and the results are reported as mean standard deviation (SD). Analysis of variance (ANOVA) was used to evaluate the influence of γ-PGA on biocompatibility. Differences with p values less than 0.05 were considered statistically significant.

Results

Osmolarity of the γ-PGA-Containing Irrigating Solution

Figure 1B:
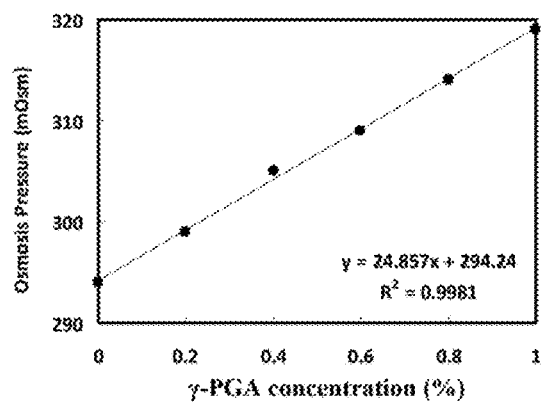

The effects of dextrose and γ-PGA on the osmolarity of the irrigating solution are shown in FIGS. 1A and 1B, respectively. Table 1 shows the compositions of dextrose-containing (FIG. 1A) and γ-PGA-containing (FIG. 1B) irrigating solutions.

TABLE 1

| Ingredient (mM) | Dextrose-containing irrigating solution | γ-PGA-containing irrigating solution |
|---|---|---|
| NaCl | 122 | 122 |
| KCl | 5.08 | 5.08 |
| CaCl$_2$ | 1.05 | 1.05 |
| MgCl$_2$ | 0.98 | 0.98 |
| NaHCO$_3$ | 25.0 | 25.0 |
| Na$_2$HPO$_4$ | 3.0 | 3.0 |
| HCl or NaOH | Adjust pH to 7.2~7.4 | Adjust pH to 7.2~7.4 |
| Dextrose | 0~1 | — |
| r-PGA | — | 0~1(%) |

Figure 1C:
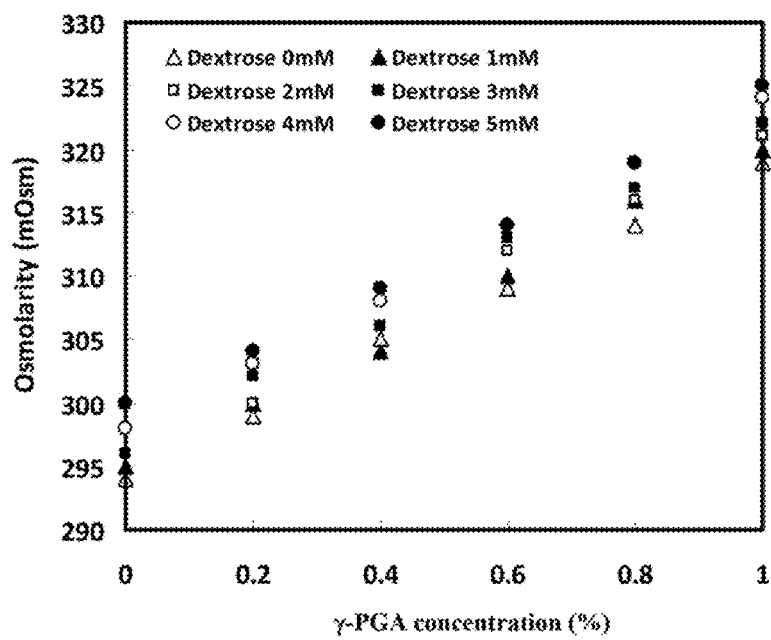

The osmolarities of the irrigating solutions containing 5 mM dextrose and 0.2, 0.4, 0.6, 0.8 and 1% γ-PGA were 304, 309, 314, 319 and 325 mOsm, respectively (FIG. 1C). When the γ-PGA concentration was decreased from 1% to 0.2%, the osmolarity of the 5 mM dextrose-containing irrigating solution decreased from 325 to 304 mOsm. However, the osmolarity of the irrigating solutions containing 1, 2, 3, 4, 5 mM dextrose without γ-PGA were 295, 296, 296, 298, 300 mOsm, respectively (FIG. 1A). Thus, dextrose had less effect on the osmolarity of the irrigating solution than γ-PGA.

Viscosity of the γ-PGA-Containing Irrigating Solution

Figure 2:
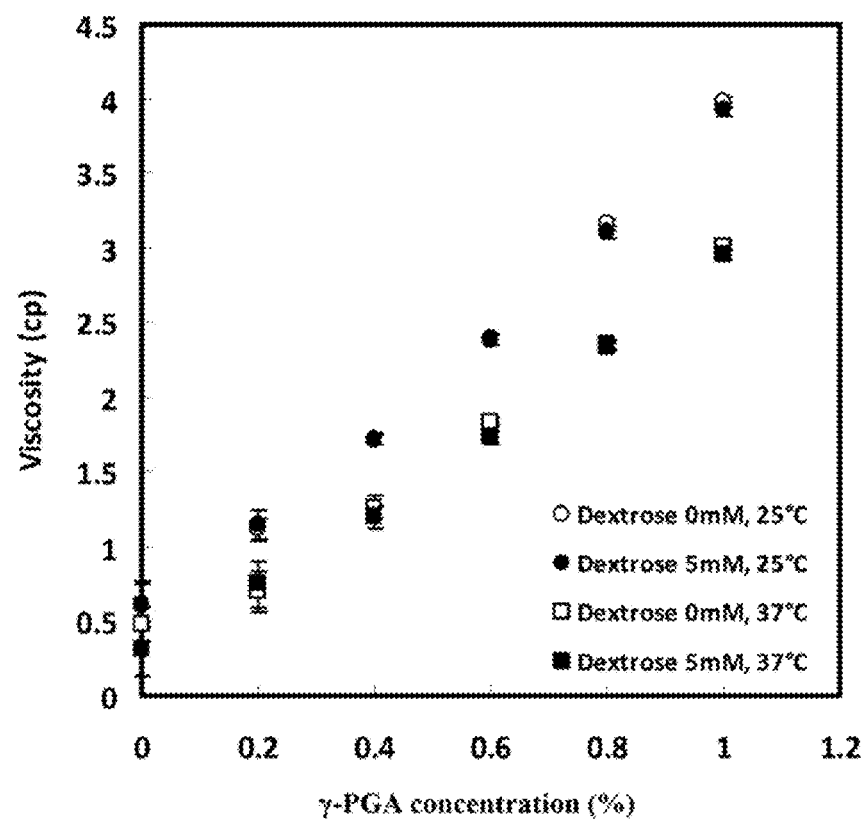
FIG. 2 is a graph showing the effect of γ-PGA on the viscosity of the irrigating solution.

FIG. 2 shows γ-PGA increased the viscosity of the irrigating solution in a concentration dependent manner and the presence of 5 mM dextrose had no impact on the viscosity. The viscosities of the irrigating solutions containing 5 mM dextrose and 0, 0.2, 0.4, 0.6, 0.8, or 1% γ-PGA at room temperature (25° C.) were 0.62, 1.15, 1.72, 2.39, 3.11, and 3.93 centipoise (cP), respectively (Table 2). The viscosity of the irrigation solution decreased when the temperature was increased to the body temperature (37° C. The viscosities of the irrigating solutions containing 5 mM dextrose and 0, 0.2, 0.4, 0.6, 0.8, or 1% γ-PGA at 37° C. were 0.32, 0.75, 1.20, 1.73, 2.33, and 2.96 cP, respectively (Table 3).

TABLE 2

| | Viscosity at 25° C. (cP) | |
|---|---|---|
| | Dextrose conc. | |
| γ-PGA (%) | 0 mM | 5 mM |
| 0 | 0.59 | 0.62 |
| 0.2 | 1.11 | 1.15 |
| 0.4 | 1.71 | 1.72 |
| 0.6 | 2.39 | 2.39 |
| 0.8 | 3.16 | 3.11 |
| 1.0 | 3.98 | 3.93 |

TABLE 3

| | Viscosity at 37° C. (cP) | |
|---|---|---|
| | Dextrose conc. | |
| γ-PGA (%) | 0 mM | 5 mM |
| 0 | 0.48 | 0.32 |
| 0.2 | 0.70 | 0.75 |
| 0.4 | 1.26 | 1.20 |
| 0.6 | 1.84 | 1.73 |
| 0.8 | 2.36 | 2.33 |
| 1.0 | 3.01 | 2.96 |

Refractive Index of γ-PGA-Containing Irrigating Solution

Figure 3:
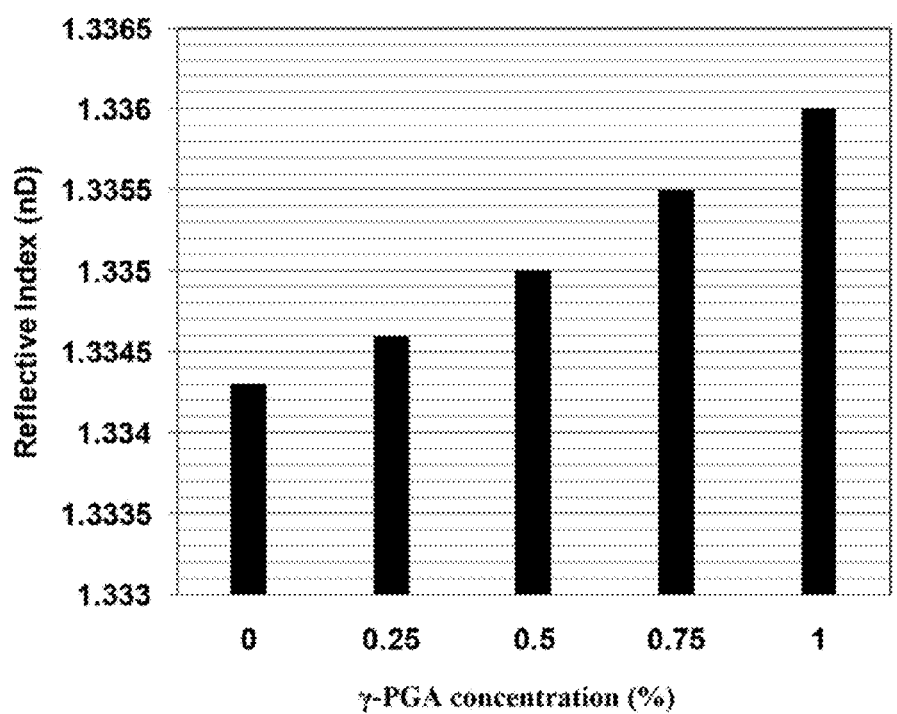
FIG. 3 is a graph showing the effect of γ-PGA on the refractive index of the irrigating solution.

The refractive indexes of the irrigating solutions containing 0.25, 0.5, 0.75 and 1% (w/v) of γ-PGA were 1.3346, 1.3350, 1.3355 and 1.3360, respectively (FIG. 3). The composition of the irrigating solution comprises 122 mM NaCl, 5.08 mM KCl, 1.05 mM CaCl$_2$, 0.98 mM MgCl$_2$, 25.0 mM NaHCO$_3$, 3.0 mM Na$_2$HPO$_4$, 0~1% (w/v) γ-PGA, and HCl or NaOH to adjust pH to 7.2~7.4.

Biocompatibility of γ-PGA

Figure 4A:
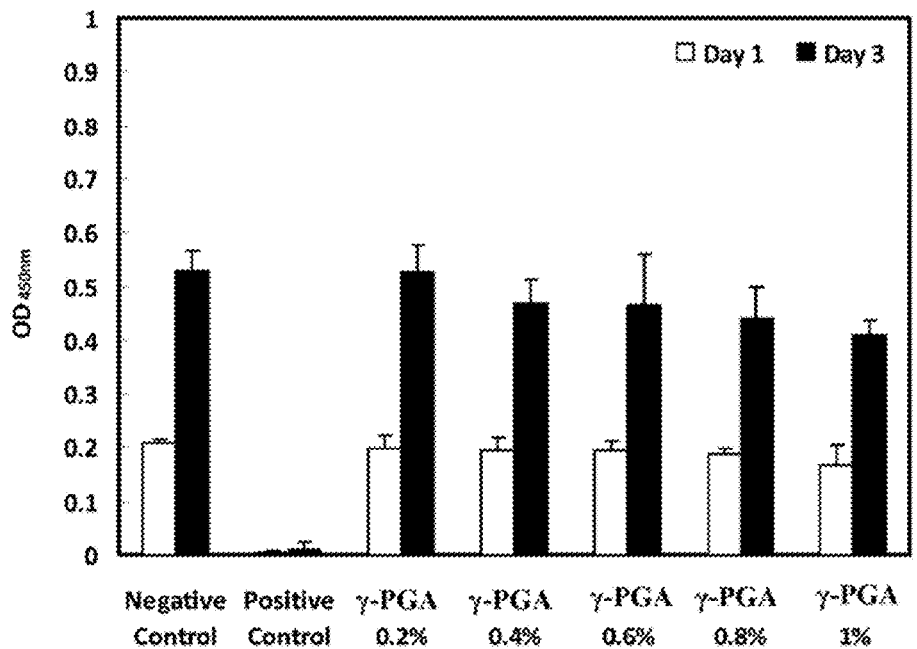
FIGS. 4A-4B show γ-PGA had no significant effect on cell proliferation. (A) bovine corneal endothelial cell. (B) human retinal pigment epithelial cells.
Figure 4B:
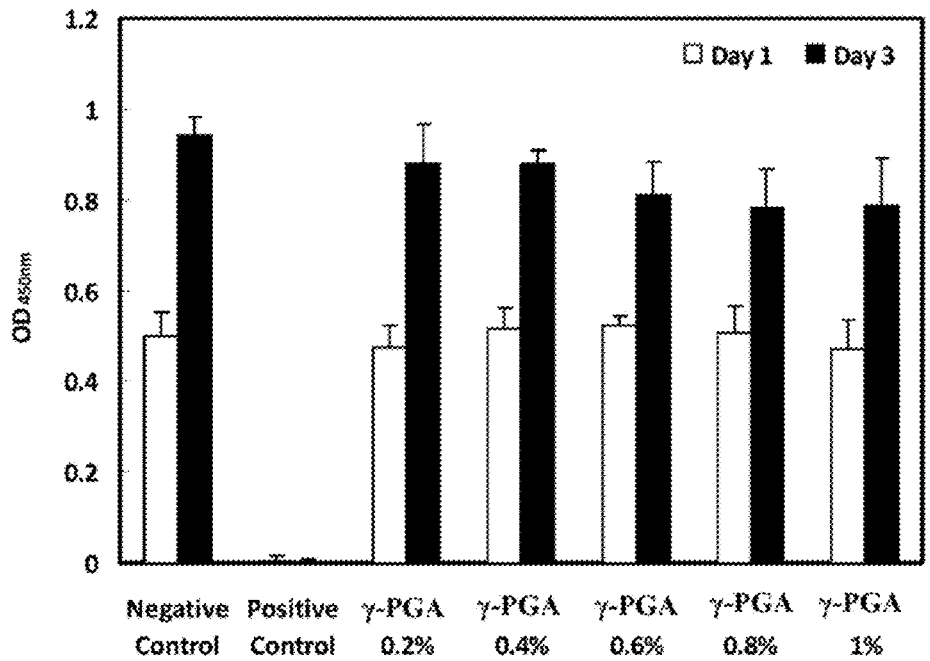

Cell viability and cytotoxicity were evaluated on bovine corneal endothelium (bCE) cells and human retinal pigment epithelium (hRPE) cells cultured in the γ-PGA-containing medium on day 1 and day 3 by WST-8 and LDH assays (FIGS. 4A-B, and FIGS. 5A-B). The WST-8 assay was used to measure the number of viable cells. The OD$_{450\ nm}$ of the medium from bCE cells treated with 0.2%, 0.4%, 0.6%, 0.8%, and 1% (w/v) of γ-PGA were 0.20±0.02, 0.19±0.02, 0.20±0.02, 0.19±0.01 and 0.17±0.04 on day 1; 0.53±0.05, 0.47±0.04, 0.46±0.10, 0.44±0.06 and 0.41±0.03 on day 3, respectively (FIG. 4A). The $OD_{450\ nm}$ of the medium from hRPE cells treated with 0.2%, 0.6%, 0.8%, and 1% γ-PGA were 0.47±0.05, 0.51±0.05, 0.52±0.02, 0.51±0.06 and 0.47±0.07 on day 1, 0.88±0.08, 0.88±0.03, 0.81±0.07, 0.78±0.09 and 0.79±0.10 on day 3, respectively (FIG. 4B). γ-PGA at a concentration from 0.2 to 1% had no effect on bCE cell and hRPE cell viability.

Figure 5A:
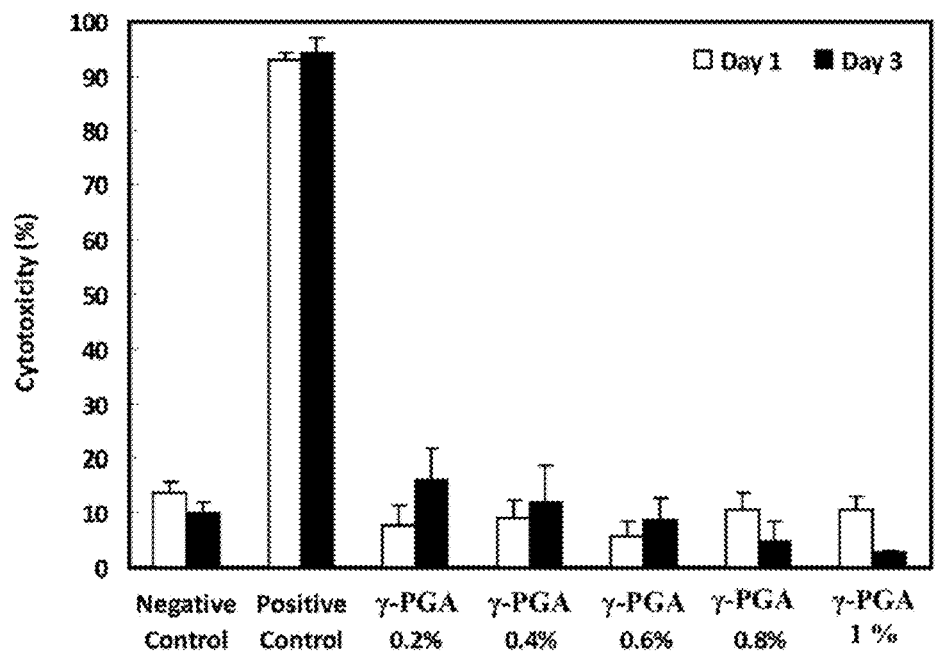
FIGS. 5A-5B show γ-PGA had no significant cytotoxic effect on cells. (A) bovine corneal endothelial cells. (B) human retinal pigment epithelial cells.
Figure 5B:
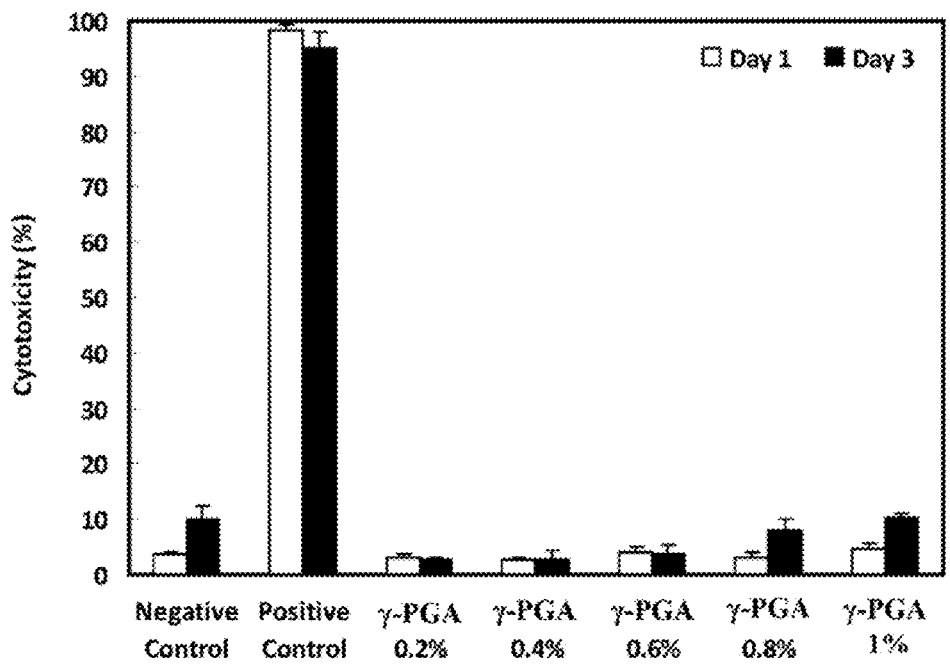
Figure 6A:
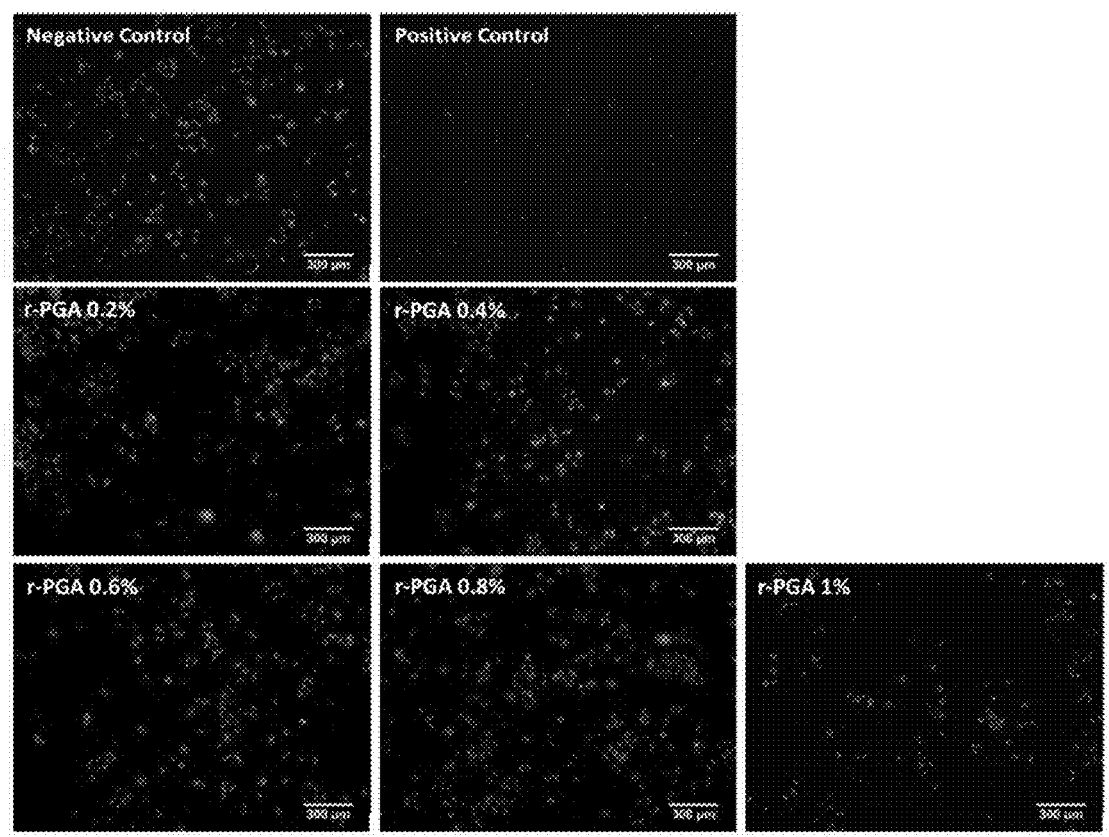
FIGS. 6-7 show a collection of photomicrographs of cells stained with dyes for simultaneous detection of viable and dead cells after culture with or without γ-PGA under a fluorescent Microscope. (6A) bovine corneal endothelial cells cultured for one day. (6B) bovine conical endothelial cells cultured for 3 days. (7A) human retinal pigment cultured for one day. (7B) human retinal pigment epithelial cells cultured for 3 days. The negative control: Alumina (Al$_2$O$_3$) extraction medium; the positive control: TRITON®-X (0.1%) in DMEM/F12 medium.
Figure 6B:
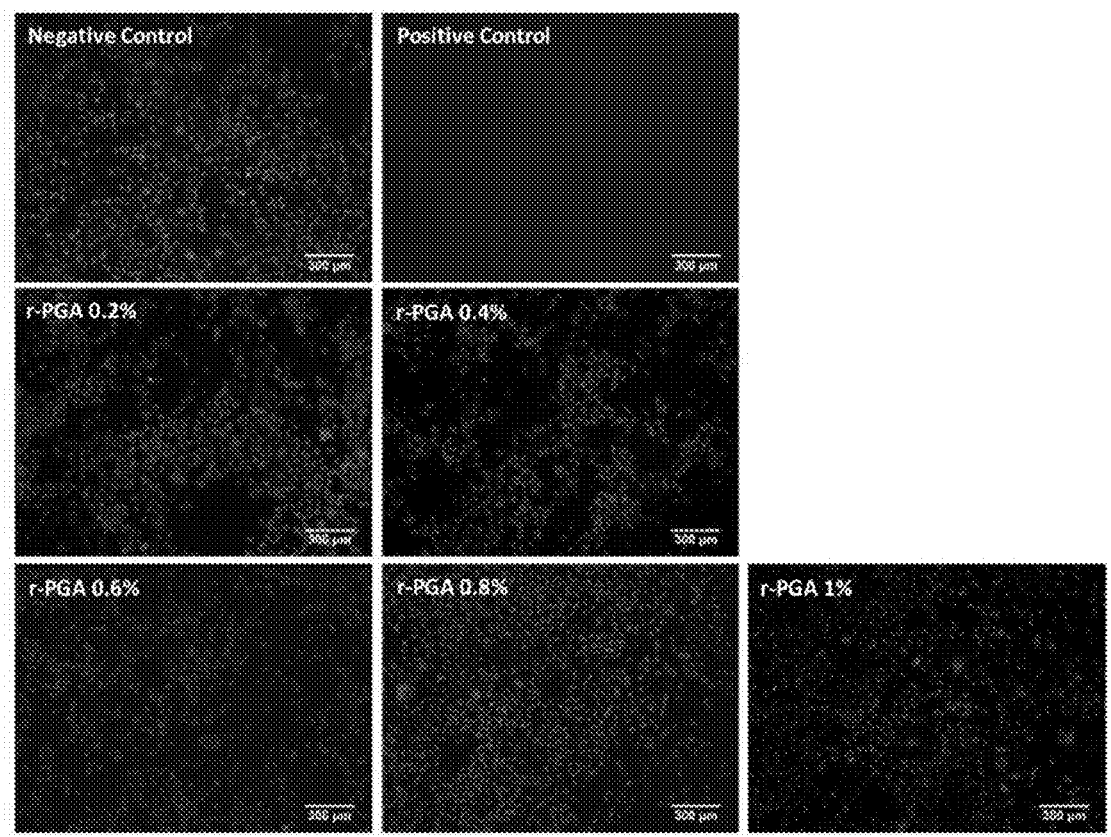
Figure 7A:
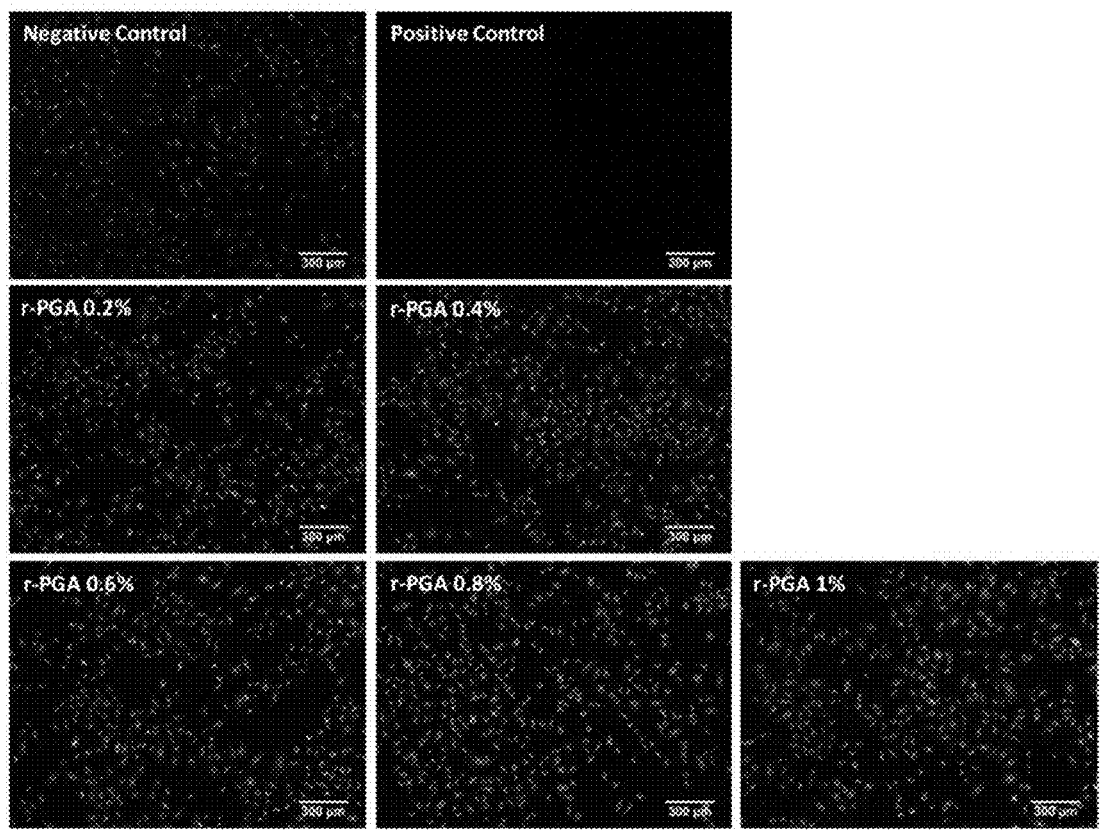
Figure 7B:
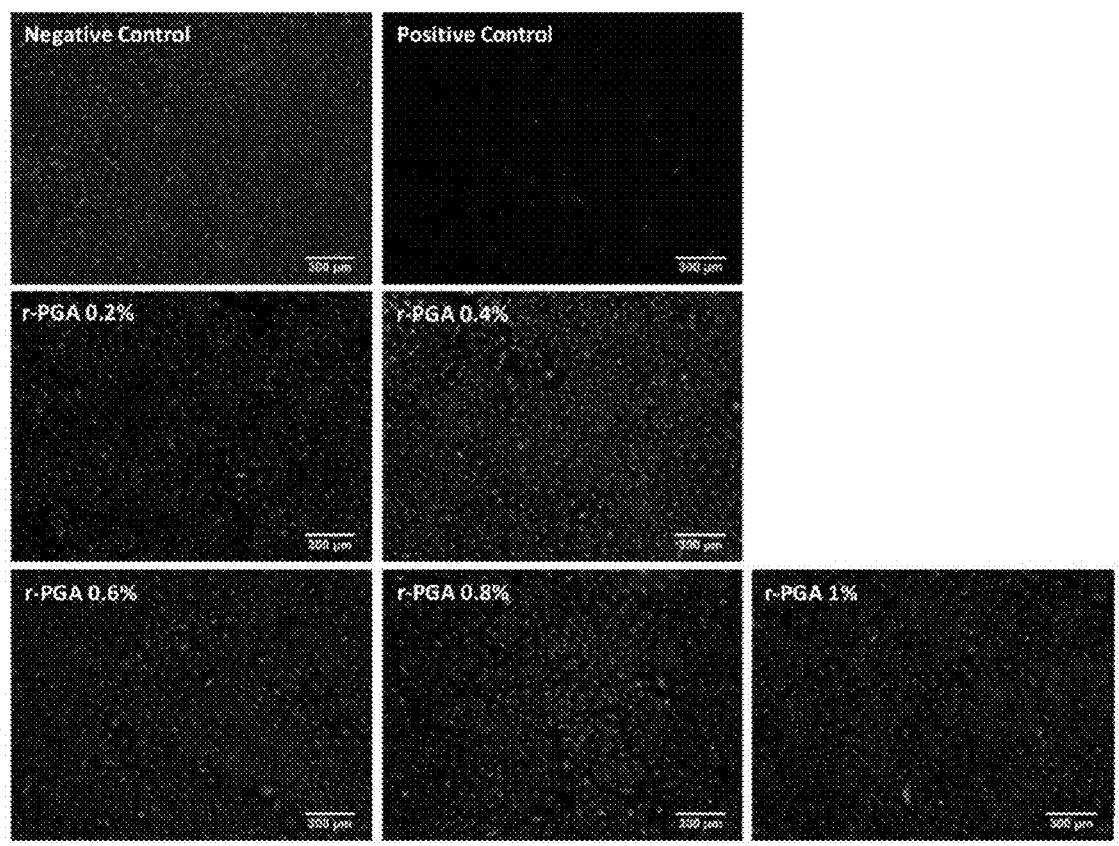

Cell death was assayed by quantifying plasma membrane damage or rupture. The LDH cytotoxicity detection is a colorimetric assay for dead and plasma membrane-damaged cells. LDH present in the culture supernatant (due to plasma membrane damage) participates in a coupled reaction which converts a yellow tetrazolium salt into a red, formazan-class dye, which is measured by absorbance at 492 nm. The amount of formazan is directly proportional to the amount of LDH in the culture medium, which is in turn directly proportional to the number of dead or damaged cells. The percentages of bCE cell cytotoxicity in the medium containing 0.2%, 0.4%, 0.6%, 0.8% and 1% γ-PGA were 7.77±3.5%, 8.90±3.5%, 5.76±2.8%, 10.86±2.8% and 10.65±2.5% on day 1; 16.11±5.8%, 12.1.1±6.6%, 8.66±4.0%, 4.61±3.7% and 2.76±0.4% on day 3, respectively. For hRPE cells, the percentages of cytotoxicity in the medium containing 0.2%, 0.4%, 0.6%, 0.8% and 1% γ-PGA were 2.97±0.6%, 2.74±0.4%, 3.95±1.0%, 2.99±1.0% and 4.78±0.9% on day 1; 2.85±0.3%, 2.77±1.5%, 3.74±1.5%, 8.11±1.9% and 10.37±0.9% on day 3, respectively. There was no significant difference between γ-PGA-containing medium and the negative control group (FIGS. 5A-B). The percentage of cell cytotoxicity represents the number of dead cells divided by the total cell number and was calculated according to the following formula:

$$\% \text{ Cytotoxicity} = \frac{\text{Medium } O.D. - \text{Blank } O.D.}{\text{Total Lysis } O.D. - \text{Blank } O.D.} \times 100.$$

Fluorescence Staining of Cells

The Live/Dead staining kit utilizes two fluorescent dyes, calcein-AM and ethidium homodimer (EthD-1). Calcein AM is a widely used green fluorescent cell marker and is membrane-permeable. Once inside the cells, Calcein AM (a non-fluorescent molecule) is hydrolyzed by intracellular esterases into negatively charged green fluorescent calcein. The fluorescent calcein is retained in the cytoplasm in live cells. It is an end-point assay for cell viability. The fluorescent signal is monitored using a 485 nm excitation wavelength and a 530 nm emission wavelength. The fluorescence signal generated from the assay is proportional to the number of living cells in the sample. Dead cells have damaged membranes. Ethidium homodimer-1 (EthD-1) enters damaged cells and is fluorescent when bound to nucleic acids. EthD-1 produces a bright red fluoresce in damaged or dead cells. Nearly all of bCE and hRPE cells were viable in γ-PGA-containing culture medium (FIGS. 6A-B and 7A-B).

Effect of γ-PGA-Containing Irrigating Solutions on Corneal Thickness

Figure 9:
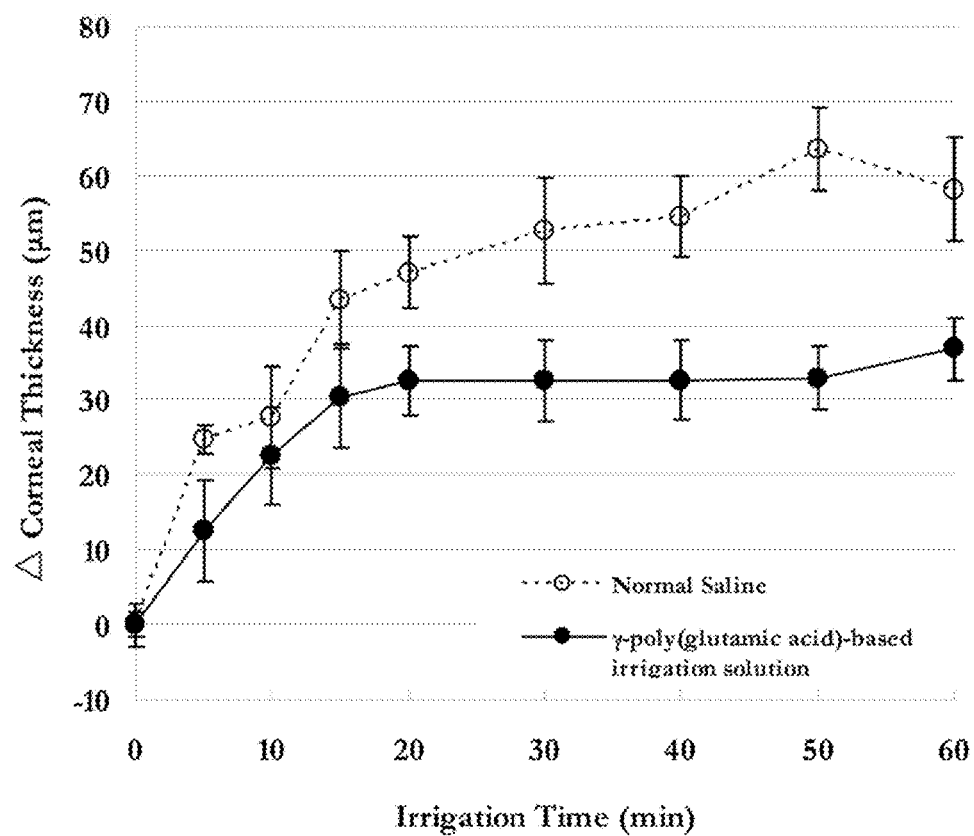
FIG. 9 is a graph showing changes in cornea thickness during the period of ocular irrigation.

Corneal thickness was measured during intraocular perfusion with the irrigating solution through two vein detained needles inserted into the eye of a rabbit (FIG. 8A). The movement of the irrigating solution was driven by a peristaltic pump (FIG. 8B). Corneal thickness was increased during the initial 20 minutes of perfusion. FIG. 9 shows the change in the corneal thickness in the group irrigated with γ-poly(glutamic acid)-based ocular solution was significantly less than that in the normal saline group. The changes in the corneal thickness in the normal saline-irrigated group and in the 0.4% (w/v) of γ-poly(glutamic acid)-containing solution-irrigated group were 47 μm and 32 μm, respectively. The initial increase in the corneal thickness might due to the injury caused by insertion of the vein detained needles. Afterwards, the cornea perfused with γ-poly(glutamic acid)-based ocular irrigation solution increased its thickness only slightly for the remaining 1 hr-perfusion with the corneal thickness swelling about 36 μm (FIG. 9). In contrast, the cornea perfused with a normal saline solution showed a continuous increase in the thickness during the remaining 60-minute perfusion with the thickness swelling about 58 μm by the end of 1 hr perfusion, which was roughly 1.6-fold increase in the corneal thickness compared with the group irrigated with γ-poly(glutamic acid)-based ocular irrigating solution.

The foregoing description of the exemplary embodiments of the invention has been presented only for the purposes of illustration and description and is not intended to be exhaustive or to limit the invention to the precise forms disclosed. Many modifications and variations are possible in light of the above teaching.

The embodiments and examples were chosen and described in order to explain the principles of the invention and their practical application so as to enable others skilled in the art to utilize the invention and various embodiments and with various modifications as are suited to the particular use contemplated. Alternative embodiments will become apparent to those skilled in the art to which the present invention pertains without departing from its spirit and scope. Accordingly, the scope of the present invention is defined by the appended claims rather than the foregoing description and the exemplary embodiments described therein.

Some references, which may include patents, patent applications and various publications, are cited and discussed in the description of this invention. The citation and/or discussion of such references is provided merely to clarify the description of the present invention and is not an admission that any such reference is "prior art" to the invention described herein. All references cited and discussed in this specification are incorporated herein by reference in their entireties and to the same extent as if each reference was individually incorporated by reference.

What is claimed is:

1. A method of protecting cornea from swelling caused by intraocular perfusion during an intraocular surgery in a patient, comprising:
    irrigating the anterior and posterior chambers of the eye of the patient with an intraocular irrigation solution comprising:
        (a) γ-polyglutamic acid (γ-PGA) and/or salt thereof; and
        (b) an ophthalmically acceptable aqueous vehicle, comprising electrolytes, a buffer, and an energy source,
    wherein the intraocular irrigation solution contains no other organic acid and has an osmolarity from 290 to 320 mOsm per Liter.

2. The method of claim 1, wherein the irrigating step further comprises perfusing corneal endothelium cells.

3. The method of claim 1, wherein the energy source is dextrose.

4. The method of claim 1, wherein the intraocular surgery is selected from the group consisting of surgical vitrectomy, cataract extraction, lens aspiration, anterior segment reconstruction and phacoemulsification.

5. The method of claim 1, wherein the irrigation solution has a viscosity of greater than 0.59 but no greater than 3.93 centipoises at a temperature of 25° C.

6. The method of claim 1, wherein the concentration of γ-PGA ranges from 0.2 to 1% (w/v).

7. The method of claim 1, wherein the concentration of γ-PGA ranges from 0.2 to 0.8% (w/v).

8. The method of claim 1, wherein the intraocular irrigation solution has a refractive index of from 1.330 to 1.344.

9. The method of claim 1, wherein the intraocular irrigation solution further comprises an antioxidant.

10. The method of claim 1, wherein the intraocular irrigation solution is free of cross-linked polyglutamic acid, and further wherein the γ-PGA is the sole polyamino acid, and the sole polymer thereof.

11. The method of claim 1, wherein the ophthalmically acceptable aqueous vehicle comprises:
(i) KCl;
(ii) NaCl;
(iii) $CaCl_2$;
(iv) $MgCl_2$;
(v) $NaHCO_3$;
(vi) $Na_2HPO_4$;
(vii) HCl or NaOH for adjusting pH to from 7.2 to 7.4;
(viii) Dextrose ranging from 0 to 5 mM; and
(ix) $H_2O$.

12. The method of claim 11, wherein the intraocular irrigation solution further comprises an antioxidant.

13. A method of irrigating anterior and/or posterior chambers of the eye of a patient having an intraocular surgery, comprising:
irrigating the anterior and/or posterior chambers of the eye of the patient with an intraocular irrigation solution in an amount sufficient to protect the cornea in the eye of the patient from an increase in thickness, the irrigation solution comprising:
(a) γ-polyglutamic acid (γ-PGA) and/or salt thereof; and
(b) an ophthalmically acceptable aqueous vehicle, comprising electrolytes, bicarbonate, and energy source,
wherein the γ-PGA is the sole polyamino acid and further wherein the irrigation solution has an osmolarity from 290 to 320 mOsm per Liter.

14. The method of claim 13, wherein the concentration of γ-PGA ranges from 0.2 to 1% (w/v).

15. The method of claim 13, wherein the concentration of γ-PGA ranges from 0.2 to 0.8% (w/v).

16. The method of claim 13, wherein the intraocular irrigating step further comprises perfusing conical endothelium cells.

17. The method of claim 13, wherein the irrigation solution further comprises an antioxidant.

18. The method of claim 13, wherein the intraocular irrigation solution contains no other organic acid, and further wherein the γ-PGA is the sole polymer thereof.

19. The method of claim 13, wherein the energy source is dextrose.

20. The method of claim 13, wherein the intraocular irrigation solution has a viscosity of greater than 0.59 but no greater than 3.93 centipoises at a temperature of 25° C.

* * * * *